(12) United States Patent
Bailey et al.

(10) Patent No.: US 8,607,634 B2
(45) Date of Patent: Dec. 17, 2013

(54) ULTRASOUND BASED METHOD AND APPARATUS TO DETERMINE THE SIZE OF KIDNEY STONE FRAGMENTS BEFORE REMOVAL VIA URETEROSCOPY

(75) Inventors: Michael Bailey, Seattle, WA (US); Joel Teichman, West Vancouver (CA); Mathew Sorensen, Seattle, WA (US)

(73) Assignees: University of Washington, Seattle, WA (US); University of British Columbia, Vancouver (CA)

( * ) Notice: Subject to any disclaimer, the term of this patent is extended or adjusted under 35 U.S.C. 154(b) by 380 days.

(21) Appl. No.: 12/469,086

(22) Filed: May 20, 2009

(65) Prior Publication Data

US 2009/0299187 A1  Dec. 3, 2009

Related U.S. Application Data

(63) Continuation-in-part of application No. 11/872,668, filed on Oct. 15, 2007.

(60) Provisional application No. 61/054,640, filed on May 20, 2008.

(51) Int. Cl.
*A61B 5/00* (2006.01)

(52) U.S. Cl.
USPC ............. 73/584; 600/437; 600/438; 600/448; 600/449; 73/597; 73/618; 73/627; 601/4

(58) Field of Classification Search
USPC ......... 600/104, 105, 135, 437, 438, 449, 448, 600/456, 463, 466; 73/584, 597, 618, 620, 73/627; 604/544; 606/127, 128
See application file for complete search history.

(56) References Cited

U.S. PATENT DOCUMENTS

| | | | |
|---|---|---|---|
| 3,606,879 A | * | 9/1971 | Estes .............................. 600/449 |
| 4,375,818 A | * | 3/1983 | Suwaki et al. ................ 600/463 |
| 4,665,751 A | * | 5/1987 | Huschelrath .................... 73/597 |
| 4,899,733 A | | 2/1990 | DeCastro et al. ................. 128/7 |

(Continued)

FOREIGN PATENT DOCUMENTS

WO  WO 2009/049148  4/2009

OTHER PUBLICATIONS

Goldberg et al. Endoluminal sonography of the urinary tract: Preliminary observations. Am J Roentgenology 1991 vol. 156 pp. 99-103.*

(Continued)

*Primary Examiner* — Unsu Jung
*Assistant Examiner* — Phong K Huynh
(74) *Attorney, Agent, or Firm* — Kilpatrick Townsend and Stockton LLP

(57) ABSTRACT

A transducer is used to send an ultrasound pulse toward a stone and to receive ultrasound reflections from the stone. The recorded time between a pulse that is reflected from the proximal surface and a pulse that is reflected either from the distal surface of the stone or from a surface supporting the stone is used to calculate the stone size. The size of the stone is a function of the time between the two pulses and the speed of sound through the stone (or through the surrounding fluid if the second pulse was reflected by the surface supporting the stone). This technique is equally applicable to measure the size of other in vivo objects, including soft tissue masses, cysts, uterine fibroids, tumors, and polyps.

26 Claims, 6 Drawing Sheets

(56) References Cited

U.S. PATENT DOCUMENTS

Figure 1A:
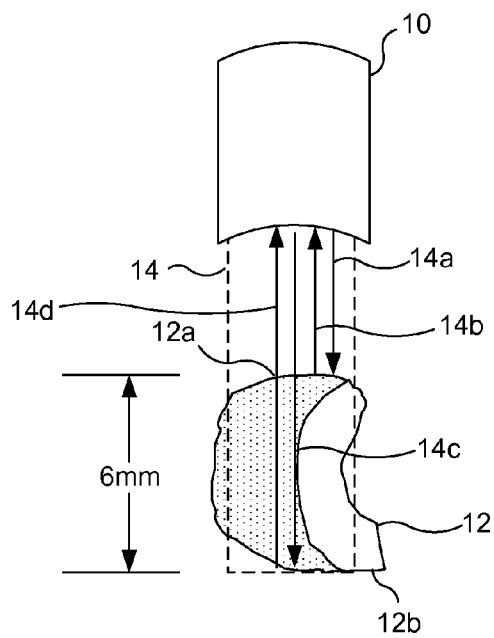

| | | | | |
|---|---|---|---|---|
| 4,942,878 | A | 7/1990 | Dory | 601/4 |
| 4,976,255 | A | 12/1990 | Reichenberger et al. | 601/4 |
| 5,209,234 | A | 5/1993 | LaRocca | |
| 6,567,688 | B1 | 5/2003 | Wang | 600/437 |
| 6,902,528 | B1 * | 6/2005 | Garibaldi et al. | 600/117 |
| 2003/0040737 | A1 | 2/2003 | Merril et al. | 606/1 |
| 2005/0033314 | A1 | 2/2005 | Sakurai et al. | 606/127 |
| 2007/0123518 | A1 | 5/2007 | Epshtein | 514/221 |

OTHER PUBLICATIONS

Chuong et al. Acoustic and Mechanical Properties of Renal Calculi: Implications in Shock Wave Lithotripsy. Journal of Endourology vol. 7 No. 6 1993 pp. 437-444.*

Schafer et al., "Design of a Miniature In-Vivo Shock Wave Hydrophone." *Ultrasonics Symposium, IEEE*: 1623-1626, 1990.

Bailey, Michael R., Yuri A. Pishchalnikov, Oleg A. Sapozhnikov, Robin O. Cleveland, James A. McAteer, Nathan A. Miller, Irina V. Pishchalnikova, Bret A. Connors, Lawrence A. Crum, and Andrew P. Evan. "Cavitation Detection During Shock-Wave Lithotripsy" Ultrasound in Med. & Biol., vol. 31, No. 9, pp. 1245-1256, Copyright 2005.

Bohris, Christian, Thomas Bayer, and Christian Lechner. "Hit/Miss Monitoring of ESWL by Spectral Doppler Ultrasound," Ultrasound in Med & Biol., vol. 29, No. 5, pp. 705-712, Copyright 2003.

Chang, C.C., S.M. Liang, Y.R. Pu, C.H. Chen, I. Manousakas, T.S. Chen, C.L. Kuo, F.M. Yu, and Z.F. Chu. "In Vitro Study of Ultrasound Based Real-Time Tracking of Renal Stones for Shock Wave Lithotripsy: Part 1," The Journal of Urology, vol. 166, 23-32, Jul. 2001.

Cleveland, Robin O., and Oleg A. Sapozhnikov. "Modeling elastic wave propagation in kidney stones with application to shock wave lithotripsy," J. Acoust. Soc. Am. 118 (4), pp. 2667-2676, Oct. 2005.

Fedele, F., A.J. Coleman, T.G. Leighton, P.R. White, and A.M. Hurrell. "Development of a new diagnostic sensor for Extra-corporeal Shock-Wave Lithotripsy," Journal of Physics: Conference Series 1 (2004), pp. 134-139. Copyright 2004.

McAteer, J.A., M.R. Bailey, J.C. Williams, Jr., R.O. Cleveland, and A.P. Evan. "Strategies for improved shock wave lithotripsy," Minerva Urologica E Nefrologica, vol. 57, N. 4. pp. 271-287, Dec. 2005.

Orkisz, M., M. Bourlion, G. Gimenez, and T.A. Flam. "Real-time target tracking applied to improve fragmentation of renal stones in extra-corporeal lithotripsy," Machine Vision and Applications (1999) 11: 138-144.

Owen, Neil R., Michael R. Bailey, Adam Maxwell, Brian MacConaghy, Tatiana D. Khokhlova, and Lawrence A. Crum. "Vibro-acoustography for targeting kidney stones during lithotripsy," J. Acoust. Soc. Am., vol. 116, No. 4, Pt. 2, p. 2509, Oct. 2004.

Owen, Neil R., Michael R. Bailey, and Lawrence A. Crum. "Characterization of a vibro-acoustography system designed to detect kidney stones during lithotripsy," J. Acout. Soc. Am., vol. 117, No. 4, Pt. 2, p. 2588, Apr. 2005.

Sapozhnikov, O.A., R.O. Cleveland, M.R. Bailey, and L.A. Crum. "Modeling of Stresses Generated by Lithotripter Shock Wave in Cylindrical Kidney Stone," Proc. Of ISTU3, ed. By J.Y. Chapelon and C. Lafon, INSERM, Lyon, 2003, pp. 323-328.

Sapozhnikov et al., "Detecting Fragmentation of Kidney Stones in Lithotripsy by Means of Shock Wave Scattering", 5th International Symposium on Therapeutic Ultrasound, Oct. 27-29, 2005, Published online May 2006, http://proceedings.aip.org/resource/2/apcpcs/829/1?isAuthorized=no, 5 pages.

* cited by examiner

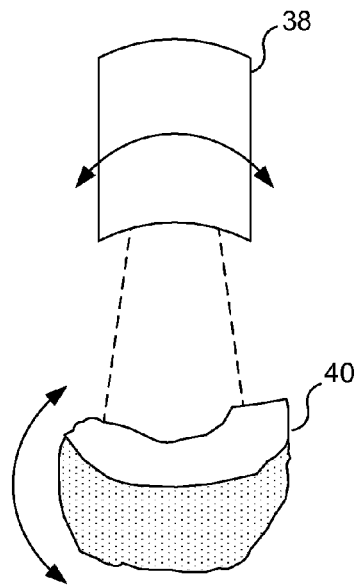
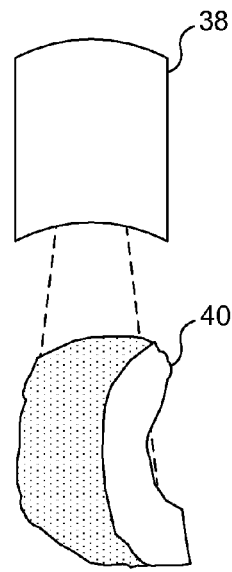
FIG. 4A  FIG. 4B
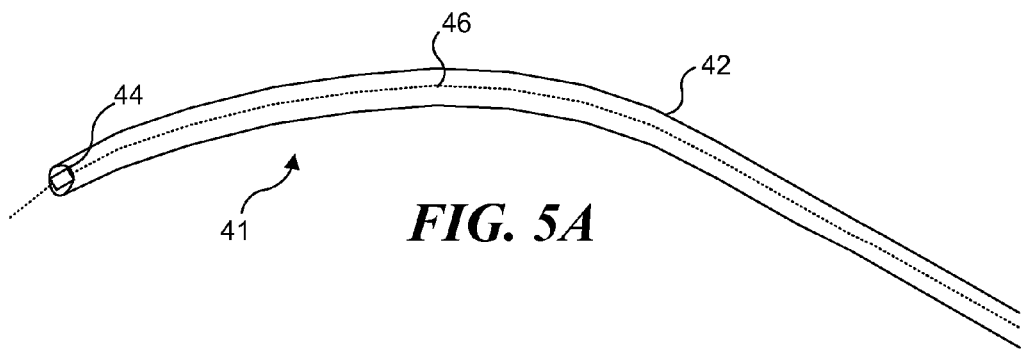
FIG. 5A
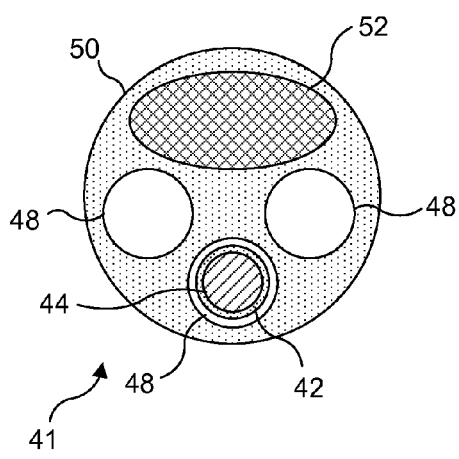
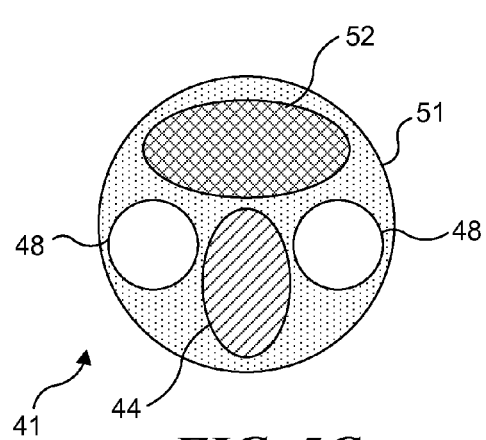
FIG. 5B  FIG. 5C

ULTRASOUND BASED METHOD AND APPARATUS TO DETERMINE THE SIZE OF KIDNEY STONE FRAGMENTS BEFORE REMOVAL VIA URETEROSCOPY

RELATED APPLICATIONS

This application is based on a prior provisional application Ser. No. 61/054,640, filed on May 20, 2008, the benefit of the filing date of which is hereby claimed under 35 U.S.C. §119 (e). This application is further a continuation in part of a prior copending application Ser. No. 11/872,668, filed on Oct. 15, 2007, the benefit of the filing date of which is hereby claimed under 35 U.S.C. §120.

GOVERNMENT RIGHTS

This invention was made with government support under grant number DK43881 awarded by National Institutes of Health (NIH) and grant number SMS00402 awarded by National Space Biomedical Research Institute (NSBRI). The government has certain rights in the invention

BACKGROUND

Ureteroscopy often requires extraction of stone fragments by grasping them in a basket and pulling them out of the body along the ureteral tract. Urologists occasionally attempt to remove such stone fragments only to find that the fragment is too large to remove through the ureter, since endoscopic stone fragment size estimates are subjective and can be in error. Currently, no intra-operative tools are available to measure fragment size before such removal is attempted. Clearly, it would be desirable to develop an approach to more accurately determine stone fragment size before an attempt is made to extract them.

SUMMARY

This application specifically incorporates by reference the disclosures and drawings of each patent application identified above as a related application.

The concepts disclosed herein employ ultrasound to enable an inter-operative tool to be used for estimating a size of an in vivo object. In an exemplary, but non-limiting embodiment and application of this novel approach, the object is a kidney stone fragment, and the inter-operative tool is a ureteroscope. In general, two echoes are detected, a first echo corresponding to a proximal surface of the object, and a second echo corresponding to a distal surface of the object (or a distal surface supporting the object). The speed of sound in the object (or the ambient fluid surrounding the distal surface supporting the object) is then used to calculate a distance between the proximal and distal surfaces of the object.

In a first variation of this technique, the source transducer is aligned such that the ultrasound pulse travels through the object, from the proximal surface to the distal surface. If the object is disposed in a fluid that effectively couples the ultrasound from the transducer to the object (such as an aqueous liquid), the transducer can be spaced apart from the object.

In a second exemplary variation of this technique, the source transducer is aligned such that a portion of the ultrasound pulse is reflected by a proximal surface of the object, and a portion of the ultrasound pulse is reflected by a distal surface supporting the object. The second variation is particularly effective when an acoustic path between the distal surface supporting the object and the ultrasound transducer is uninterrupted.

While the concepts disclosed herein can be beneficially employed to determine the size of kidney stone fragments during a ureteroscopic procedure, it should be recognized that these concepts can also be used to estimate the size of other objects during an inter-operative procedure, including but not limited to, the size of stones in the pancreatic tract, the size of stones in the gall bladder, the size of stones in bile ducts, the size of stones in salivary ducts, and the size of in vivo tissue objects (including but not limited to cysts, fibroids, tumors, and polyps).

The transducer employed can be incorporated into a distal end of an inter-operative instrument (such as a ureteroscope), or can be incorporated into a distal end of elongate flexible body delivered through a working lumen of an inter-operative instrument. It should be understood that, depending on the in vivo location and the procedure being implemented, the ultrasound transducer can be incorporated into the distal end of a probe that does not need to be sized to fit through a lumen of another instrument.

It should be noted that while the use of ultrasound (i.e., sound above the range of human hearing, generally accepted to be sound having a frequency of greater than about 20,000 Hz) represents an exemplary embodiment, it should be recognized that similar results theoretically could be obtained using different frequencies not normally associated with the term ultrasound. In general, higher frequencies are preferred, as lower frequencies are less directive, pulses at lower frequencies are longer, so more processing is required to identify a small time difference between two long signals, and long low frequency signals don't scatter well off of small objects (leading to weaker signals).

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Figure 1B:
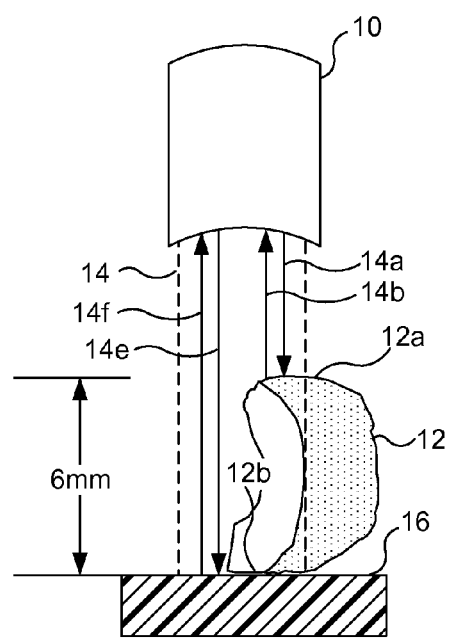
Figure 2A:
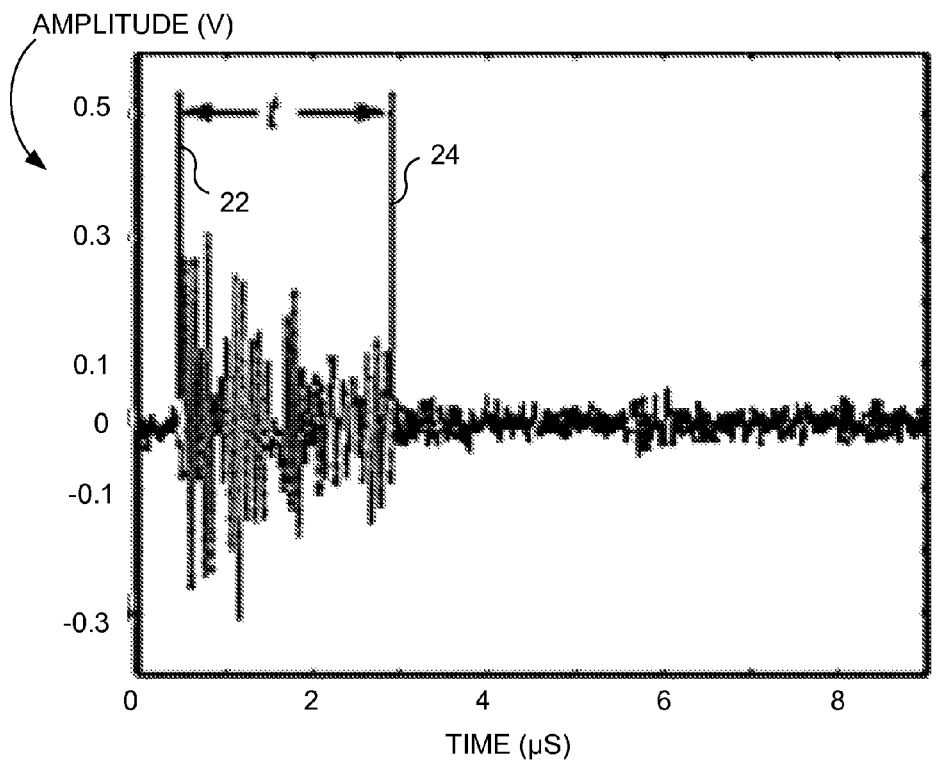
Figure 2B:
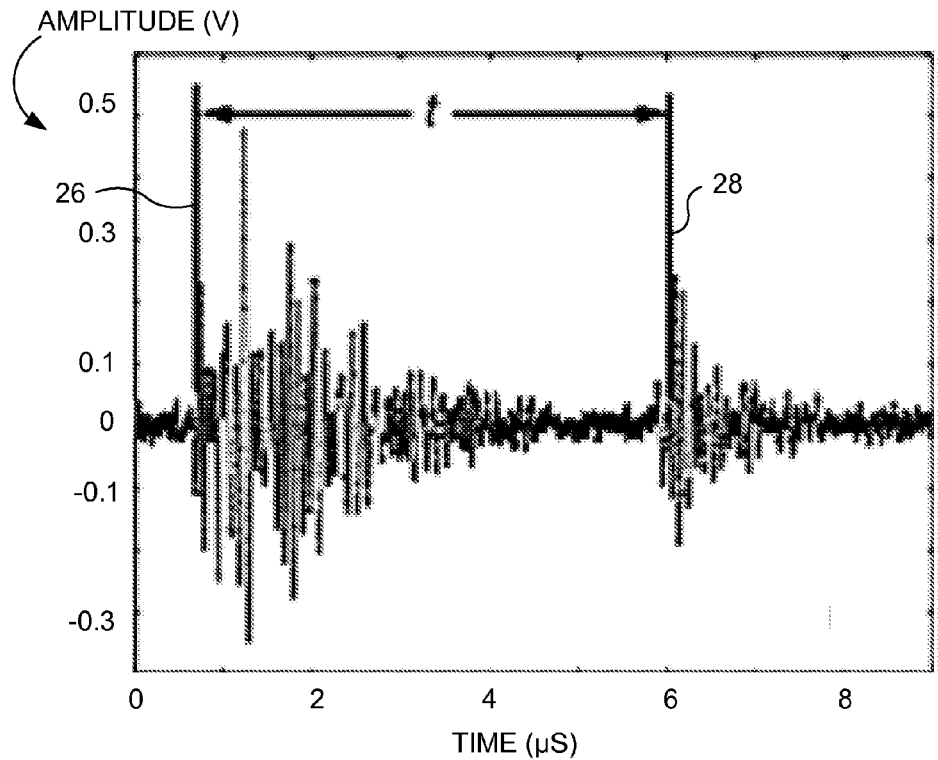
Figure 3:
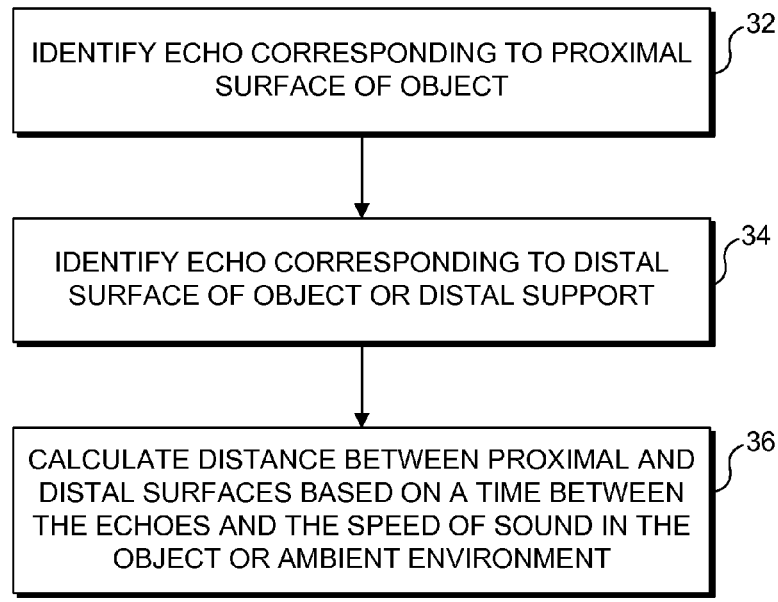
Figure 6A:
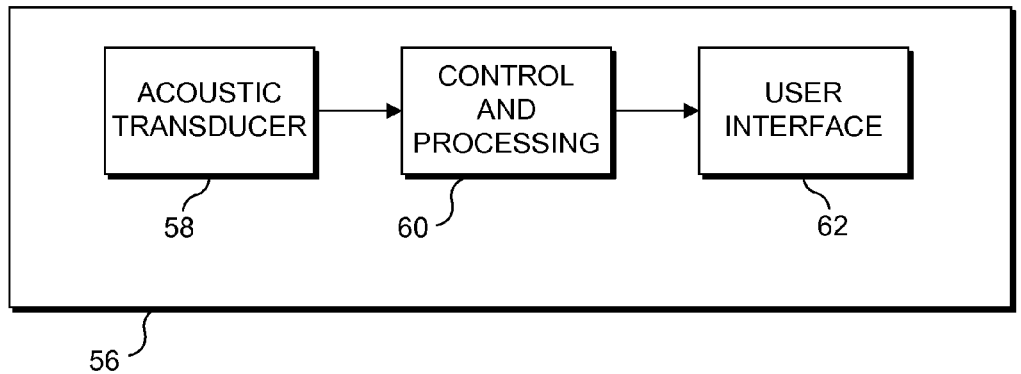
Figure 6B:
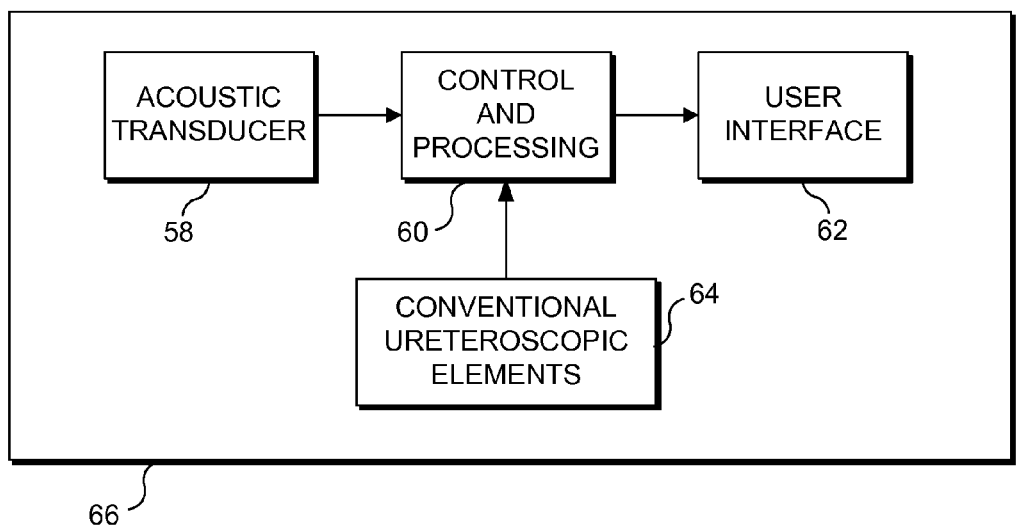
Figure 7A:
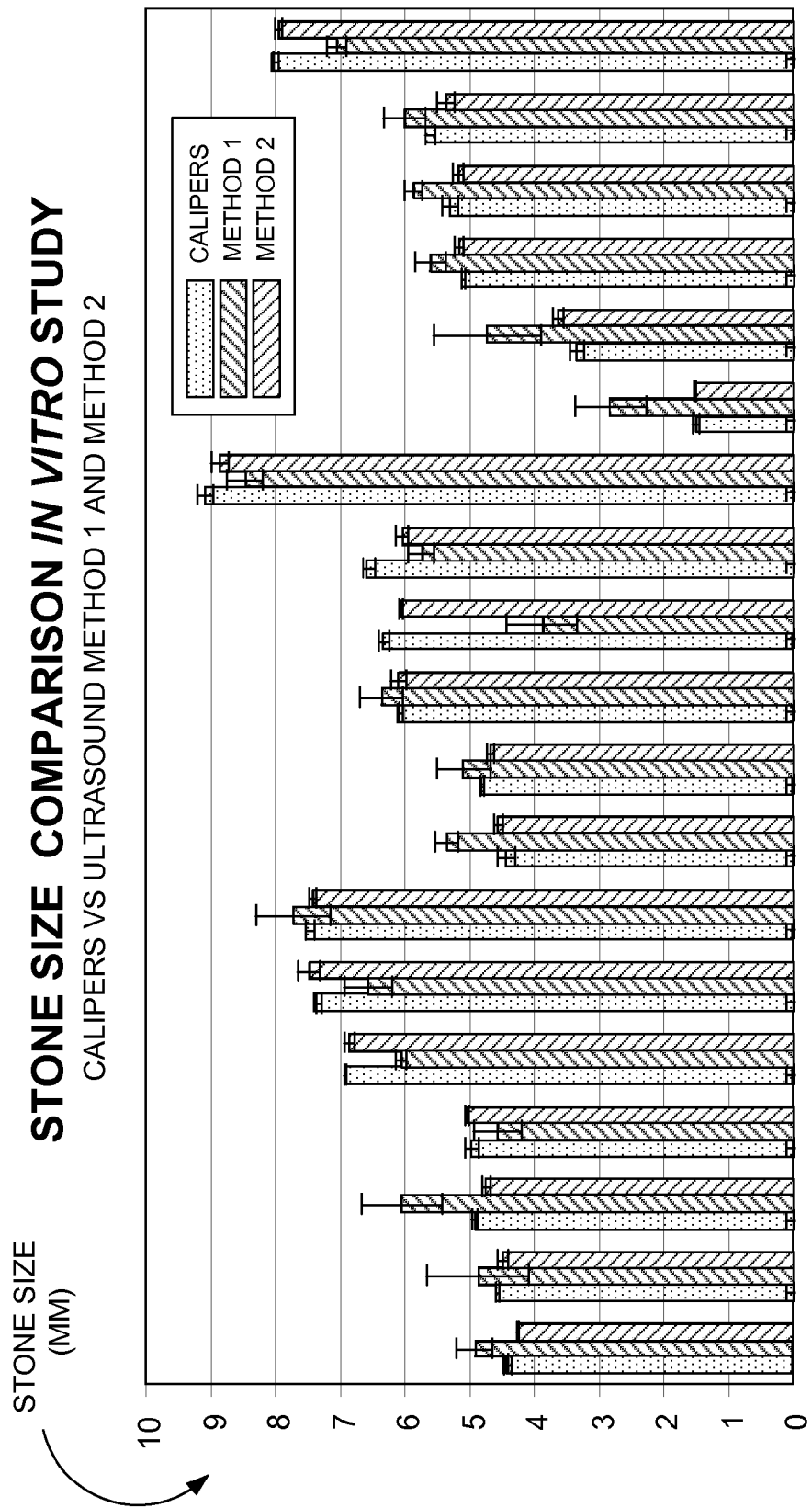
Figure 7B:
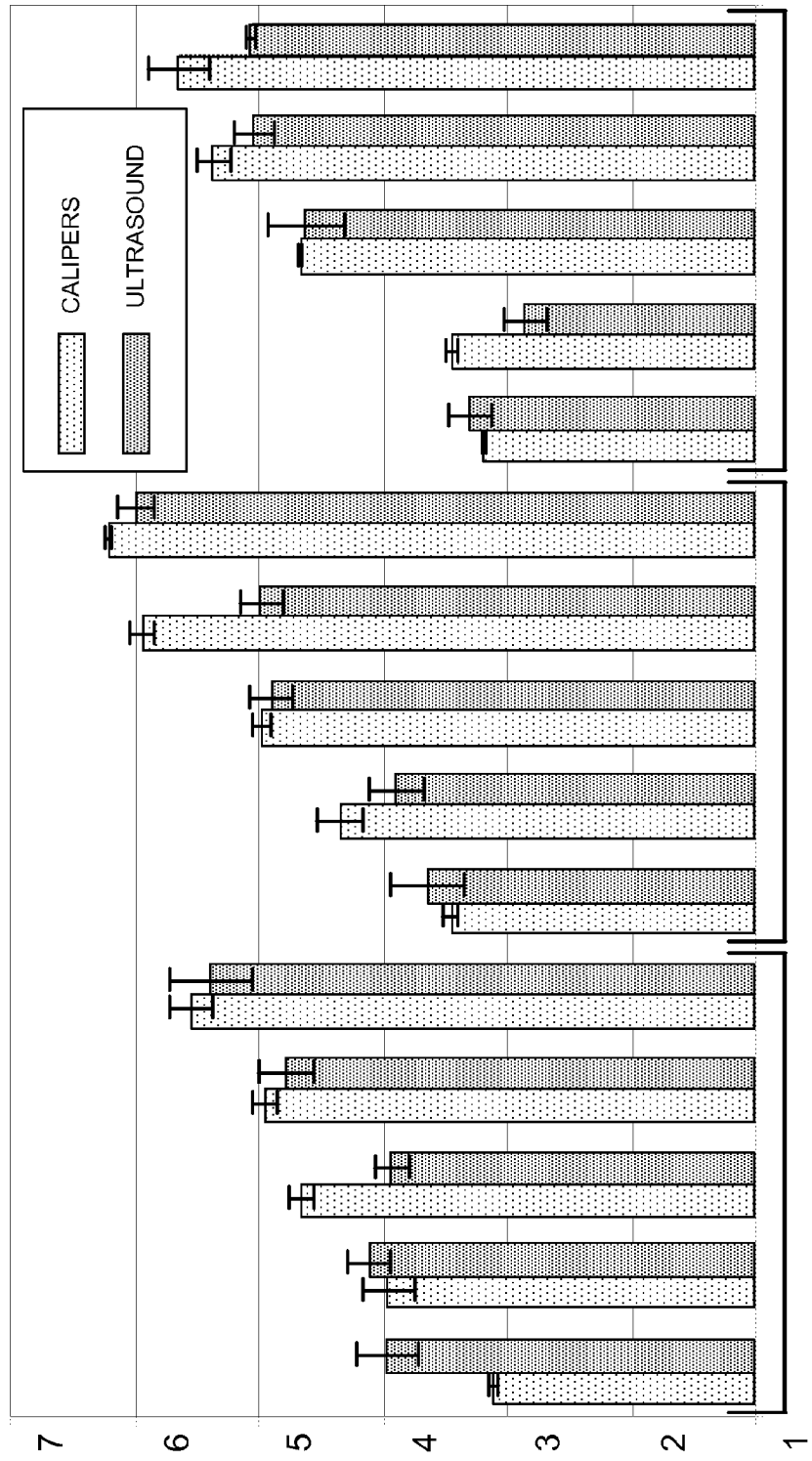

Various aspects and attendant advantages of one or more exemplary embodiments and modifications thereto will become more readily appreciated as the same becomes better understood by reference to the following detailed description, when taken in conjunction with the accompanying drawings, wherein:

FIG. 1A schematically illustrates a first exemplary embodiment employing the concepts disclosed herein, wherein ultrasound is used to determine a size of an in vivo object during an operative procedure, and wherein the size is calculated based on a speed of sound in the object, and a time interval between a first echo collected from a proximal surface of the object, and a second echo collected from a distal surface of the object;

FIG. 1B schematically illustrates a second exemplary embodiment employing the concepts disclosed herein, wherein ultrasound is used to determine a size of an in vivo object during an operative procedure, and wherein the size is calculated based on a speed of sound in ambient fluid surrounding the object, and a time interval between a first echo collected from a proximal surface of the object, and a second echo collected from a distal surface supporting the object;

FIG. 2A graphically illustrates empirical data collected using the embodiment of FIG. 1A;

FIG. 2B graphically illustrates empirical data collected using the embodiment of FIG. 1B;

FIG. 3 is a flowchart including exemplary steps for implementing either embodiment of FIGS. 1A and 1B;

FIGS. 4A and 4B schematically illustrate an exemplary and optional additional technique for manipulating the object before implementing one of the ultrasound sizing techniques disclosed herein, to ensure that a maximum dimension of the object will be measured;

FIG. 5A schematically illustrates an exemplary medical device for implementing the ultrasound sizing techniques disclosed herein, comprising an elongate flexible body, with an ultrasound transducer disposed at a distal end of the device;

FIG. 5B schematically illustrates a first exemplary embodiment of the medical device of FIG. 5A, wherein the medical device is inserted into a working lumen of a flexible ureteroscope, to enable a size of kidney stones (and kidney stone fragments) to be measured during a ureteroscopic procedure;

FIG. 5C schematically illustrates a second exemplary embodiment of the medical device of FIG. 5A, wherein the medical device is based on a flexible ureteroscope, modified to include an ultrasound transducer at its distal end, to enable a size of kidney stones (and kidney stone fragments) to be measured during a ureteroscopic procedure;

FIG. 6A schematically illustrates an exemplary system for using the medical device of FIG. 5B;

FIG. 6B schematically illustrates an exemplary system for using the medical device of FIG. 5C;

FIG. 7A graphically illustrates a first set of in vitro empirical data comparing measurements collected using calipers, the embodiment of FIG. 1A, and the embodiment of FIG. 1B; and FIG. 7B graphically illustrates a second set of in situ empirical data comparing measurements collected using calipers, the embodiment of FIG. 1A, and the embodiment of FIG. 1B.

DESCRIPTION

Figures and Disclosed Embodiments are Not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

As noted above, the concepts disclosed herein employ ultrasound to enable a medical tool to estimate a size of an in vivo object. In an exemplary, but non-limiting embodiment, the object is a kidney stone or fragment thereof, and the inter-operative tool is a ureteroscope. Kidney stones or stone fragments are often removed through narrow tubes during ureteroscopy. Thus, one aspect of the concepts described herein is a device to measure stone size before attempting to remove a stone or stone fragment that is too large to fit through an available lumen. Attempting to extract a stone that is too large wastes time and increases the chance of injuring biological passages, such as the ureter. In general, the technique disclosed herein employs an ultrasound element that is sufficiently small to be incorporated into a distal end of a ureteroscope, or sufficiently small to be advanced through a working lumen of a ureteroscope, to send ultrasound and also receive ultrasound reflections from the object, whose size is to be measured (for ureteroscopy, the object will normally be a stone or stone fragment). The time between reflections collected from the proximal and the distal surfaces of the object, along with the speed of sound, are used to calculate the object size. The speed of sound can be that in the stone or in the surrounding fluid, depending on how the medical practitioner orients the ultrasound instrument.

It should be noted that while the present novel approach of measuring the size of kidney stones (or fragments thereof) during ureteroscopy represents an exemplary embodiment, the concepts disclosed herein can also be used to measure the size of other types of in vivo objects, including, but not limited to, mineral deposits and stones in the gall bladder, in the salivary tract, and in the biliary tract. Furthermore, the same novel concepts can be used to measure tissue-based in vivo objects, including, but not limited to, cysts, polyps, uterine fibroids, tumors, and other tissue masses, as well as foreign objects (such as objects that have been swallowed or otherwise ingested, and objects that have been intentionally or un-intentionally introduced into a patient's body during a medical procedure). Ultrasound transducers for sizing purposes can be incorporated into many different types of medical instruments, in addition to ureteroscopes, such as catheters, surgical tools, biopsy, endoscopic and laparoscopic tools, and medical probes. As discussed in greater detail below, the design of existing medical tools can be modified to include an ultrasound transducer, or a separate tool having the transducer disposed at its distal end can be fabricated for use during a medical procedure.

FIG. 1A schematically illustrates a first exemplary embodiment embodying the novel concepts disclosed herein, wherein ultrasound is used to determine a size of an in vivo object during an operative procedure. The size of the object is calculated based on a speed of sound in the object, and a time interval between a first echo collected from a proximal surface of the object, and a second echo collected from a distal surface of the object.

Referring to FIG. 1A, an ultrasound transducer 10 is disposed adjacent to an object 12 (such as a kidney stone) so that ultrasound energy propagates generally along a path 14. So long as the ambient environment conducts ultrasound waves, the transducer need not be in contact with the object. Bodily fluids such as water, blood, and urine will conduct ultrasound waves with less loss than tissue. When the ultrasound transducer is energized, a portion 14a of the ultrasound pulse encounters a proximal surface 12a of the object, causing an echo or reflection 14b to return to the transducer for collection. Similarly, a portion 14c of the ultrasound pulse passes through the object and encounters a distal surface 12b of the object, causing an echo or reflection 14d to return to the transducer for collection. In an empirical study discussed in detail below, this technique was successfully used to measure stones that were approximately 6 mm in length, but this size should not be construed as a limitation.

Thus, in this first exemplary illustration, the source transducer is aligned such that the ultrasound pulse travels through the object, from the proximal surface to the distal surface. The distance between the proximal and distal surfaces is calculated using the following relationship:

$$D = c_1 t/2 \quad (1)$$

where t is the time between the two reflected pulses, D is the distance between the proximal and distal surfaces, and $c_1$ is the speed of sound in the object.

Note that dividing by 2 in Eq. (1) is required because the pulse passes through the object once, is reflected from the distal surface, and passes back through the object a second time. Where the object is a kidney stone, $c_1$ can be assumed to be 4300 m/s (although as will be discussed in detail below, useful measurements were also obtained using 3000 m/s for $c_1$). The speed of sound in different types of stones does vary, and if the specific type of stone is known, the speed of sound for that type of stone can be used. However, the empirical studies discussed below indicate that useful sizing results can be obtained using an estimated value for $c_1$. Where the object is a tissue mass (such as a cyst, a tumor, or a polyp), $c_1$ can be assumed to be 1540 m/s. The speed of sound in different types of tissue also varies, and if the speed of sound for a specific tissue type is known, that value can be employed for improved accuracy.

FIG. 1B schematically illustrates a second exemplary embodiment embodying the concepts disclosed herein, wherein ultrasound is used to determine a size of an in vivo object during an operative procedure. However, in this embodiment, the object size is calculated based on a speed of sound in ambient fluid surrounding the object, and a time interval between a first echo collected from a proximal surface of the object, and a second echo collected from a distal surface supporting the object.

Referring to FIG. 1B, ultrasound transducer 10 is disposed adjacent to an object 12 (such as a kidney stone), but offset such that ultrasound pulses reflect from both a proximal surface of the object and a distal surface supporting the object. As with the exemplary embodiment of FIG. 1A, when the ultrasound transducer is energized, a portion 14a of the ultrasound pulse encounters a proximal surface 12a of the object, causing an echo or reflection 14b to return to the transducer for collection. However, because of the orientation of the transducer, a portion 14e of the ultrasound pulse passes through the ambient fluid alongside the object and encounters a distal surface 16 that supports the object, causing an echo or reflection 14f to return to the transducer for collection.

Thus, in this second exemplary embodiment employing the novel sizing technique, the source transducer is aligned such that a portion of the ultrasound pulse is reflected by a proximal surface of the object and a portion of the ultrasound pulse is also reflected by a distal surface supporting a distal surface of the object. The distance between the proximal and distal surfaces of the object can then be calculated using the following relationship:

$$D = c_2 t/2 \qquad (2)$$

where t is the time between the two reflected pulses, D is the distance between the proximal and distal surfaces, and $c_2$ is the speed of sound in the ambient fluid surrounding the object.

Again, dividing by 2 in Eq. (2) is required because the transmitted pulse passes alongside the object once, is reflected from the distal surface supporting the object, and passes back alongside the object a second time. Where the object is a kidney stone, $c_2$ can be assumed to be 1481 m/s (the speed of sound in water—urine in practice) at 20 degrees Celsius. Empirical studies indicate that useful sizing results can be obtained using this value for $c_2$. Where the object is disposed in a different fluid environment, the speed of sound for that fluid can be used for $c_2$ (so long as the fluid is capable of propagating an ultrasound pulse). Note that this second variation is particularly effective when an acoustic path between the distal surface supporting the object and the ultrasound transducer is uninterrupted. In an in vivo environment where an acoustical path from the transducer to a distal surface supporting the object is obstructed, the first exemplary embodiment is likely to be more readily implemented. It will be appreciated that if the speed of sound for the ambient fluid can be determined or estimated with greater accuracy than the speed of sound in the object, then the measurements from the second exemplary embodiment are likely to be more accurate (assuming that either embodiment can be used without any difficulty).

With respect to the exemplary embodiment of FIG. 1B, it should be noted that the parameters noted above are based on the object resting on a distal surface (such as tissue) and being surround by a fluid (such as blood or urine). In cases where the object is surrounded by tissue, the exemplary embodiment of FIG. 1A will likely be more useful, unless the tissue surrounding the object is different than the tissue supporting the object. If the tissue surrounding the object is contiguous with the tissue supporting the object, then there will be no interface at the distal surface to reflect the acoustic pulse when implementing the exemplary embodiment of FIG. 1B.

FIG. 2A graphically illustrates empirical data collected using the exemplary embodiment of FIG. 1A for a particular stone. From the signal, a first peak 22 is identified as being indicative of the first reflection at the proximal surface of the object, and a second peak 24 is identified as being indicative of the second reflection at the distal surface of the object.

It should be noted that identifying the peaks must take into consideration the following factors. The overall signal includes a reflection from the proximal and distal surfaces of the stone, as well as reflections from any internal structure in the stone. The signal is further complicated by extra reverberation inherent in the stone and the transducer. Finally, the interrogation pulse from the transducer has a certain duration. For example, the empirical data for the ex vivo testing was collected using a relatively short interrogation pulse of ~5 cycles of the transducer source frequency. Consider the analogy of a person trying to generate an echo by yelling; one generally shouts "echo" rather that just "O". Clearly, the duration of the "echo" interrogation pulse is longer than the duration of the "O" interrogation pulse. To continue with that analogy, the time interval that is required is the time interval between a first "echo" (from the proximal surface) and a second "echo" (from the distal surface) in response to the "echo" interrogation pulse. The time interval between the "e" in the first "echo" (from the proximal surface) and the "o" in the second "echo" (from the distal surface) is referred to as the total duration. Ideally, one would be able to extract from the signal the time (i.e., the location of a peak) for the "e" in the first "echo" (from the proximal surface) and the "e" in the second "echo"; i.e., the starting time for each echo. Because the first and second echoes can overlap in time, identifying those peaks from a signal can require signal processing as opposed to simply visually identifying peaks from a graphical display of the signal. For example, the "e" in the second "echo" (from the distal surface) might actually be received at the same time as the "h" in the first "echo" (from the proximal surface). Because of this issue, the data collected in the ex vivo testing determined the time interval using the total duration, as opposed to specifically identifying the beginning of the first and second echoes. Significantly, even such an approximation provided useful results. A subsequent study (discussed below) employed signal processing techniques to extract the beginning of the first and second echoes from the signal.

FIG. 2B graphically illustrates empirical data collected using the embodiment of FIG. 1B (from the same stone for which data collected using the embodiment of FIG. 1A is graphically displayed in FIG. 2A). Again, a first peak 26 is indicative of the first reflection at the proximal surface of the object, and a second peak 28 is indicative of the second reflection at the distal surface supporting the object. As discussed above, in the first ex vivo study the total duration was employed, as opposed to using signal processing techniques to determine more precise locations for the beginning of the first and second echoes, thus such peaks in FIGS. 2A and 2B are simply intended to generally indicate the locations of the beginning of the first and second echoes. Note that t measured with the embodiment of FIG. 1A is roughly half that measured with the embodiment of FIG. 1B, because the sound speed in a kidney stone (the embodiment of FIG. 1A) is roughly twice that of the sound speed in water (the embodiment of FIG. 1B).

FIG. 3 is a flowchart including exemplary steps for implementing either of the embodiments of FIGS. 1A and 1B. In a step 32, an echo caused by reflection of an ultrasound pulse from a proximal surface of an object is identified in an ultrasound signal. In a step 34, an echo caused by reflection of the ultrasound pulse from either a distal surface of the object or a distal surface supporting the object (as described above) is identified in the received ultrasound signal. In a step 36, a time between the two echoes and a speed of sound in the object or in the ambient fluid are used to calculate a distance between the proximal and distal surfaces, providing an indication of a size of the object.

It should be recognized that the distance being measured is axial or one dimensional (i.e., a height, width, or length), while the object is three dimensional. Although in some circumstances, any dimensional information about the object will be more useful than no information, preferably, the dimension being measured should represent a maximum dimension of the object. FIGS. 4A and 4B schematically illustrate an exemplary and optional additional technique for manipulating the object before implementing one of the exemplary ultrasound sizing techniques disclosed herein, to ensure that a maximum dimension of the object is measured. An optical instrument 38 can be used to enable a user to view an object 40, and thereby determine if the object or the optical instrument needs to be repositioned so that a maximum dimension of the object is aligned with the optical instrument. Of course, the intent is to ensure that the ultrasound pulses propagate generally along the axis that is aligned with longest dimension of the object. Accordingly, after such repositioning (if required), the ultrasounds transducer is then placed in the same relative position as the optical instrument, which will achieve the alignment of the ultrasound pulse propagation path in alignment with the axis of the longest dimension of the object. In practice, the optical instrument and the ultrasound transducer can be located adjacently on a distal end of a single medical instrument (such as a ureteroscope), disposed adjacently proximate the object, or can be disposed in adjacent lumens of an elongate medical instrument, such as a catheter. Further, the optical instrument (such as a digital sensor or an optical fiber coupled to a digital sensor or an eyepiece) can be advanced through a working lumen of a medical instrument to enable the object's relative position to be visualized and corrected if needed, then removed, such that the ultrasound transducer is then advanced through the same lumen and is not oriented relative to the object to measure the maximum dimensional size of the object. Note that using a single lumen for visualization and sizing may be useful even when a relative position of the stone or instrument is not manipulated. Furthermore, when using a ureteroscope a urologist can generally discern two dimensions (i.e., height and width) to visually estimate the size. However, a third dimension, depth, is much harder to determine, and the stone may even be partially buried an unknown depth into tissue. The concepts disclosed herein can be used to measure such depth.

FIG. 5A schematically illustrates an exemplary medical device 41 for implementing the ultrasound sizing techniques disclosed herein. This exemplary medical device includes an elongate flexible body 42, with an ultrasound transducer 44 disposed at a distal end of the device. Depending on the location at which the medical device will be used, the medical device may (or may not—as appropriate) be designed to be used with a guidewire 46.

FIG. 5B schematically illustrates a first exemplary embodiment of medical device 41 of FIG. 5A, wherein the medical device is inserted into a working lumen 48 of a flexible ureteroscope 50, to enable a size of kidney stones (and kidney stone fragments) to be measured during a ureteroscopic procedure. Note that as shown, flexible ureteroscope 50 includes a plurality of working lumens (though only one working lumen is required), and an optical element 52 (generally an imaging sensor, although some such instruments may employ optical fibers coupled to a remote eyepiece or image sensor). In ureteroscopes, the working lumens generally average about 3 Fr (based on the French catheter scale chart, i.e., about 1 mm). Thus, for use with ureteroscopes, medical device 41 of FIG. 5A should be about 2.5 Fr (i.e., about 0.8 mm). Of course, applications of the present approach in other in vivo locations will have other sizing requirements. Providing ultrasound transducers of sufficient power, in sizes as small as 0.5 mm does not present any significant technical challenge. It should be recognized that the relative sizes, shapes, and locations of the elements shown in FIG. 5B are intended to be exemplary, and not limiting.

FIG. 5C schematically illustrates a second exemplary embodiment of medical device 41 of FIG. 5A, wherein the medical device is based on a flexible ureteroscope 51, modified to include ultrasound transducer 44 at its distal end, to enable the size of kidney stones (and kidney stone fragments) to be measured during a ureteroscopic procedure. Thus, in this embodiment, medical device 41 itself comprises flexible ureteroscope 51, which includes a plurality of working lumens (though only one working lumen is required), optical element 52 (generally an imaging sensor, although such instruments may employ optical fibers coupled to a remote eyepiece or image sensor), and ultrasound transducer 44. It should be recognized that the relative sizes, shapes, and locations of the elements shown in FIG. 5C are intended to be exemplary, and not limiting.

FIG. 6A schematically illustrates an exemplary system 56 for using the medical device of FIG. 5B. The system includes a medical device with an ultrasound transducer 58 at its distal end, control and processing element 60, and a user interface 62 (generally a display, although it should be recognized that other types of user interfaces, such as audible outputs, can also be beneficially employed). A personal computer or other type of computing device represents an exemplary control and processing component, although it should be recognized that other types of logical processing components can also be employed, such as custom logic circuits and application specific integrated circuits (ASICs). Processing element 60 at least enables the distance calculations discussed above to be automatically performed in response to collection of the ultrasound data (the paired echoes corresponding to reflections from the proximal and distal surfaces of the object, or from the proximal surface of the object and the backing surface that supports the distal surface of the object). In at least one exemplary embodiment, the user interface is configured to enable a user to enter a value used for the speed of sound in a particular object (or in a particular ambient fluid), or to select a value that will be used for this parameter from a plurality of options. In at least one other exemplary embodiment, processing element 60 performs the calculations using a default value for the speed of sound.

FIG. 6B schematically illustrates a similar exemplary system 66 for using the medical device of FIG. 5C. The system includes the modified ureteroscope with an ultrasound transducer 58 at its distal end, control and processing element 60, user interface 62 (generally a display, although it should be recognized that other types of user interfaces, such as audible outputs, can also be beneficially employed), and additional conventional ureteroscopic components 64. It will be appreciated that in using exemplary system 66 in connection with treating a medical condition in which a stone has formed in a patient's body, one of a number of accepted medical procedures, such as lithotripter shock waves, or laser light, will often be used to initially break the stone into a plurality of smaller fragments. The novel concept disclosed herein can then be used for measuring the size of the stone fragments to assist the medical practitioner in removing the stones through a lumen. If any stone fragment is measured and found to be too large to be removed, the procedure for fragmenting the stones may be applied again to further fragment the too large fragments, until all are of sufficiently small size to be removed through the lumen.

FIG. 7A graphically illustrates a first set of empirical data comparing measurements collected using calipers, the embodiment of FIG. 1A, and the embodiment of FIG. 1B, while FIG. 7B graphically illustrates a second set of empirical data comparing measurements collected using calipers, the embodiment of FIG. 1A, and the embodiment of FIG. 1B.

First Empirical Study (In Vitro)

The initial study was an in vitro study using excised kidney stones. A 10 MHz, 10 Fr transducer was used to send an ultrasound pulse toward the stone, and was also used to receive ultrasound reflections from the stone. The time between the reflections from the proximal and the distal ends of the stone was used to calculate the stone size, generally as discussed above. For this initial study, the speed of sound in the stones measured in the study was assumed to be 3000 m/s. Note that both techniques discussed above were implemented (i.e., where the second reflection was due to an echo from the distal surface of the stone, and where the second reflection was due to an echo from a distal surface supporting the distal side of the stone). The size of the stone was also measured using calipers (along the same axis measured using the ultrasound techniques).

The measurements were performed for 19 human stones, and compared by linear regression. Single stones from 19 separate patients were obtained from a stone reference laboratory. All stones were >95% pure composition. Three different types of stones (seven calcium oxalate monohydrate, six cystine, and six calcium hydrogen phosphate dihydrate), of a variety of shapes were rehydrated for 24 hours in de-ionized water. Each stone was measured three times using measurements with calipers; mean and standard deviation were recorded; and then, the stone was placed in the same orientation on a planar tissue phantom and submerged in 20° C. water.

The 10 MHz (⅛" diameter/10 Fr) transducer (Model M112™, available from Panametrics NDT (now Olympus NDT) of Waltham Mass.) transmitted and received ultrasound pulses through a pulser receiver (Model 5072PR™, Olympus NDT) at 100 Hz. The signals produced in response to the received pulses were displayed in real time on a digital oscilloscope. The operator aligned the transducer by hand and recorded three signals for each method (i.e., the respective exemplary embodiments of FIGS. 1A and 1B). The operator aligned the transducer visually, but made final position decisions by watching the oscilloscope and aligning the transducer to capture the longest time intervals. The signals were then analyzed by another investigator in a blind study to determine the time used to calculate stone size. A regression analysis between mean measurements with the calipers and ultrasound-based measurements was used to compare the data. These results are graphically presented in FIG. 7A. It should be recognized that well-known signal processing techniques can be employed to automate the process of calculating the time interval between reflections. Such signal processing can include, but is not limited to, subtraction of background interference, averaging to increase a signal to noise, de-convolution to remove an initial pulse length, and cross correlation to determine the time between the two reflections.

The embodiment of FIG. 1B (second echo reflecting from a distal surface supporting the stone) was somewhat easier to implement. Time determination for the embodiment of FIG. 1A (second echo reflecting from a distal surface of the stone itself) was more difficult to implement because of multiple scattering and reverberations within the stone. For the embodiment of FIG. 1A (second echo reflecting from a distal surface of the stone), the correlation between stone size determined with calipers and ultrasound-determined stone size was $r^2=0.71$ ($p<0.0001$), and in two stones, the deviation was greater than 1 mm. For the embodiment of FIG. 1B (second echo reflecting from a distal surface supporting the stone), the correlation was better, with $r^2=0.99$ ($p<0.0001$).

Significantly, both the embodiment of FIG. 1A and the embodiment of FIG. 1B provided useful measurements, although the results provided by the embodiment of FIG. 1B were more accurate and precise. The measurement error (i.e., precision, indicated by error bars in FIG. 7A) was less than 0.2 mm in all stones using the embodiment of FIG. 1B, and less than 1 mm in all stones using the embodiment of FIG. 1A. Accuracy was similar to the precision, except in two stones where the embodiment of FIG. 1B was in error more than 1 mm. There was no obvious consistent bias due to stone type, which could have been exhibited in measurements from the embodiment of FIG. 1A, where differences in the speed of sound in different stone types could have introduced such a bias (for example, the measurements would be lower than the true values, if the actual speed of sound in the objects were greater than 3000 m/s).

Based on the first empirical (in vitro) study, medical instrument-based ultrasound can accurately and precisely measure stone fragment size using either of the two exemplary techniques (i.e., the embodiments of FIGS. 1A and 1B). Significantly, accurate measurements were obtained when holding the transducer by hand, indicating that hand-held instruments should provide accurate measurements as well. The transducer employed (10 Fr, 30 mm) was larger than can be employed in a ureteroscope, and the signal obtained was on the magnitude of one volt. Using a smaller transducer for clinical use will reduce the signal magnitude, but it should be possible to reduce the signal well below the one volt level and still obtain data sufficient in magnitude to make an accurate measurement. This novel technique thus provides acceptable real-time fragmentation size measurements during ureteroscopy, as well as being usable for sizing other in vivo objects.

Second Empirical Study (In Situ)

The second study was carried out in situ using excised kidney stones implanted in a porcine liver. Significantly, while a smaller transducer was employed, useful measurements were still obtained, thereby confirming that the novel approach should provide the desired results when in clinical use.

In the in situ study, a 1.2 mm (3.6 Fr) ultrasound-based instrument was used to accurately and precisely measure stone fragments deep within the collecting system of a porcine kidney. In this study, 15 human stones of three types (five each of calcium oxalate, cystine, calcium phosphate), and having a variety of shapes, ranging in size from 3-7 mm, were rehydrated and placed deep in the collecting system of the lower pole of a freshly-sectioned porcine kidney. The speed of sound for the three stone types was determined using a separate reference stone. The 2 MHz, 3.6 Fr needle hydrophone was used to send and capture ultrasound pulses. The transit signal time, t, through the stone (or ambient fluid) was measured, and along with the speed of sound in the stone (or the ambient fluid), c, the thickness of each stone was calculated as explained above. Calculated stone thicknesses were compared to measurements with digital calipers. The results are graphically presented in FIG. 7B.

The speed of sound measured for the calcium oxalate stones was 4,331 m/s (±48), the speed of sound measured for the cystine stones was 4,321 m/s (±44), and the speed of sound measured for the calcium phosphate stones was 4,266 m/s (±75). A stone size was determined for all 15 stones using measurements with calipers and the embodiments of FIGS. 1A and 1B, generally as described above. Correlation between ultrasound-determined thickness and measurements with the calipers was excellent ($r2=0.90$, $p<0.0001$). Overall, ultrasound measurements underestimated stone size by 3%, but performed equally well in all three stone types. All stone measurements were accurate to within 1 mm, and 10 (66%) stone measurements were accurate within 0.5 mm.

It should be noted that in the first empirical study (i.e., the ex vivo study), it was assumed that the speed of sound in the human kidney stones was 3000 m/s, and rather than processing the signal to specifically identify the beginning of the first and second echoes, the total duration of the first and second echoes was employed. In the second empirical study (i.e., the in situ study), the speed of sound in the different stone types was actually measured before the stones were implanted in the porcine kidney, and signal processing techniques were employed to specifically identify the beginning of the first and second echoes. While the techniques employed in the second empirical study (i.e., the in situ study) provided more accurate results, it is significant to note that the approximations employed in the first empirical study (i.e., the ex vivo study) introduced only a minor amount of error, such that useful results were provided using the techniques in the first empirical study (i.e., the ex vivo study). In the second empirical study (i.e., the in situ study), the beginning of the first and second echoes were determined by de-convolving the basic shape of the pulse from the echo signal detected (the artisan of ordinary skill will be familiar with such processing).

All calculations of signal transit time used to determine stone thickness were performed using signals processed to remove background noise and interference (caused by the initial excitation of the transducer to produce the pulse before the transducer is used to receive the pulse). Note that additional signal processing may further improve accuracy and facilitate automation of measurements. As noted above, additional signal processing can include averaging to increase a signal to noise, de-convolution to remove an initial pulse length, and cross correlation to determine the time between the two reflections.

Significantly, in both the in vitro and in situ studies, the ultrasound signals were captured in real time, and processed offline. Real time processing is certainly achievable, since the calculations do not require significant computational resources. Once the calculations are performed, the result can be visually displayed to a user, or audibly output to a user, in real time.

While smaller instruments are generally preferable, and as a result, a single transducer will be employed in many embodiments, it should be recognized that a first acoustic emitter and a second acoustic receiver could also be employed. Measurements might also be done from orthogonal directions to better estimate a maximum dimension without reorienting/repositioning the object or a single ultrasound transducer.

While the concepts disclosed herein should be particularly well suited for use in the removal and treatment of in vivo mineral stones, it should be recognized that such concepts can also be beneficially applied in measuring the size of discrete masses of soft tissue (or of a foreign object present in the body). The medical fees for many procedures, such as treatment of a tumor, are based on a size of the tissue mass, thus the techniques disclosed herein will enable tumor size to be easily and accurately determined during a medical procedure, for determining billings.

With respect to the claims that follow, the term "approximately" should be considered to encompass a stated value, plus or minus 10%.

As discussed above, while the use of ultrasound (i.e., sound above the range of human hearing, generally accepted to be sound having a frequency of greater than about 20,000 Hz) represents an exemplary implementation, it should be recognized that similar results could possibly be obtained using different frequencies not normally associated with the term ultrasound. Thus, in the claims that follow, the more general terms acoustic transducer, acoustic energy and acoustic pulse have been employed.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A method for determining a size of an in vivo kidney stone, comprising the steps of:
   (a) using an in vivo device comprising an acoustic transducer to detect:
      (i) a first signal generated in response to an interrogation pulse, the first signal comprising a first reflected acoustic wave that is reflected from a proximal surface of the in vivo kidney stone and a second reflected acoustic wave that is reflected from a distal surface of the in vivo kidney stone; and
      (ii) a second signal generated in response to the interrogation pulse, the second signal comprising a reflected acoustic wave that is reflected from a tissue supporting the distal surface of the in vivo kidney stone and that is only passed through an acoustical path from the support tissue to the acoustic transducer, the acoustical path positioned through a material alongside and outside the in vivo kidney stone and distal of the proximal surface of the kidney stone, the material comprising a fluid or a tissue which has a different composition than the support tissue; and
   (b) processing the first and second signals to identify the first reflected acoustic wave and the acoustic wave reflected from the support tissue and processing the identified reflected acoustic waves to determine the size of the in vivo kidney stone, as a function of a time interval between the first reflected acoustic wave and the acoustic wave reflected from the support tissue and a speed of sound in the acoustical path material, and wherein the speed of sound in the acoustical path material is different than a speed of sound through the in vivo kidney stone.

2. A method for determining a size of an in vivo object, comprising the steps of:
   (a) advancing a medical device including an acoustic transducer to a position that is proximate to the in vivo object such that an acoustical path between the acoustic transducer and a distal surface supporting the in vivo object is unobstructed, the acoustical path through a material adjacent to and outside of the in vivo object, the speed of sound through the material differing from the speed of sound through the in vivo object;
   (b) directing an interrogation pulse of acoustic energy from the acoustic transducer toward the in vivo object and the distal support surface;
   (c) collecting a first signal generated in response to the interrogation pulse, the first signal comprising a first reflected acoustic wave that is reflected from a proximal surface of the in vivo object and a second reflected acoustic wave that is reflected from a distal surface of the in vivo object;
   (d) collecting a second signal generated in response to the interrogation pulse, the second signal comprising a reflected acoustic wave that is reflected from the distal support surface and that is only passed through the acoustical path; and
   (e) automatically processing the first and second signal to identify the first reflected acoustic wave and the acoustic wave reflected from the distal support surface to determine the size of the in vivo object, as a function of a time interval between the collection of the first reflected acoustic wave and the acoustic wave reflected from the distal support surface, and the speed of sound in the acoustical path material.

3. The method of claim 2, wherein the material comprises a bodily fluid surrounding the in vivo object.

4. The method of claim 3, wherein the speed of sound in the material is assumed to be approximately 1480 m/s.

5. The method of claim 2, wherein the step of advancing a medical device including an acoustic transducer to the location that is proximate to the in vivo object comprises the step of advancing the medical device including the acoustic transducer through a working lumen of a flexible ureteroscope.

6. The method of claim 2, wherein the step of advancing a medical device including an acoustic transducer to the location that is proximate to the in vivo object comprises the step of advancing a flexible ureteroscope that includes the acoustic transducer to the location.

7. The method of claim 2, further comprising the step of enabling an operator to view a spatial orientation of the in vivo object relative to the medical device, to further enable the spatial orientation to be manipulated to ensure that the size determined corresponds to a maximum dimension of the in vivo object.

8. The method of claim 2, further comprising the step of enabling an operator to enter a value to be used for the speed of sound in the material, wherein the value is used to determine the size of the in vivo object.

9. The method of claim 2, further comprising the step of presenting at least one indication of the size of the object to an operator, the at least one indication being selected from the group consisting of:
   (a) an audible indication; and
   (b) a visual indication.

10. The method of claim 2, wherein the in vivo object is selected from the group consisting of:
   (a) a kidney stone;
   (b) a gall stone;
   (c) a stone present in a salivary tract;
   (d) a stone present in a biliary tract;
   (e) a pancreatic stone; and
   (f) a vascular stone.

11. The method of claim 2, wherein the in vivo object comprises a discrete soft tissue mass.

12. A medical system for determining a size of an in vivo object, the system comprising:
   (a) a probe having a distal end configured to be positionable proximate to the in vivo object, the probe including an acoustic emitter for emitting an interrogation pulse of acoustic energy and an acoustic receiver for collecting reflected acoustic energy; and
   (b) a controller configured to determine the size of the in vivo object by implementing the following functions:
      (i) identifying a first signal generated in response to the interrogation pulse, the first signal comprising a first echo corresponding to acoustic energy reflected from a proximal surface of the in vivo object and a second echo corresponding to acoustic energy reflected from a distal surface of the in vivo object;
      (ii) identifying a second signal generated in response to the interrogation pulse, the second signal comprising an echo corresponding to acoustic energy that is reflected from a surface supporting the in vivo object and that is only passed through material alongside and outside the in vivo object, a speed of sound in the material alongside the in vivo object being not equal to a speed of sound through the in vivo object;
      (iii) processing the first and second signal to identify the first echo and the echo corresponding to acoustic energy reflected from the support surface; and
      (iv) determining the size of the in vivo object as a function of a time interval between collection of the first echo and the support surface echo, and the speed of sound in the material alongside the in vivo object.

13. The system of claim 10, wherein the probe comprises an elongate flexible body sized and configured for insertion through a working lumen of a ureteroscope.

14. The system of claim 10, wherein the probe comprises a ureteroscope having an optical element, the acoustic emitter, and the acoustic receiver all disposed proximate its distal end.

15. The system of claim 10, wherein the acoustic emitter and the acoustic receiver comprise a single acoustic transducer.

16. A ureteroscopic system configured to determine a size of an in vivo kidney stone, comprising:
   (a) an elongate flexible body;
   (b) an optical element that enables a user to view the in vivo kidney stone;
   (c) at least one acoustic element for emitting interrogation pulses and collecting acoustic energy; and
   (d) a controller configured to determine the size of the kidney stone by implementing the following functions:
      (i) identifying a first signal generated in response to an interrogation pulse, the first signal comprising a first echo corresponding to acoustic energy reflected from a proximal surface of the kidney stone and a second echo corresponding to acoustic energy reflected from a distal surface of the kidney stone;

(ii) identifying a second signal generated in response to the interrogation pulse, the second signal comprising an echo corresponding to acoustic energy that is reflected from a surface supporting the kidney stone and that is only passed through material alongside and outside the kidney stone, a speed of sound through the material alongside the kidney stone being less than a speed of sound through the kidney stone; and (iii) determining the size of kidney stone as a function of a time interval between the collection of the first echo and the support surface echo, and the speed of sound in the material alongside the kidney stone.

17. An in vivo technique for treating a stone, comprising the steps of:
(a) introducing a medical probe to a location that is proximate to the stone and any fragments produced by breaking the stone such that an acoustical path from the medical probe to a surface supporting a distal surface of the stone or a fragment is unobstructed; and
(b) determining a size of the stone or the fragment, such that any fragment too large to be removed is broken into smaller fragments; the size of each stone or fragment being determined by performing the following steps:
  (i) directing an acoustic interrogation pulse from the medical probe toward the stone or fragment being sized;
  (ii) identifying a first signal generated in response to the interrogation pulse, the first signal comprising a first echo corresponding to acoustic energy reflected from the proximal surface of the stone or fragment being sized and a second echo corresponding to acoustic energy reflected from the distal surface of the stone or fragment being sized;
  (ii) identifying a second signal generated in response to the interrogation pulse, the second signal comprising an echo corresponding to acoustic energy that is reflected from the surface supporting the stone or fragment and that is only passed through material alongside and outside the stone or fragment being sized, a speed of sound through the material is less than a speed of sound through the stone or fragment; and
  (iii) determining the size of stone or fragment as a function of a time interval between the collection of the first echo and the support surface echo, and the speed of sound in the material alongside the stone or fragment being sized.

18. The method of claim 11, wherein the discrete soft tissue mass is selected from the group consisting of:
(a) a cyst;
(b) a uterine fibroid;
(c) a tumor; and
(d) a polyp.

19. The method of claim 1, further comprising, positioning the in vivo device relative to the in vivo kidney stone such that the acoustical path is unobstructed.

20. The method of claim 1, further comprising reducing interference from the first and second signal caused by an initial excitation of the transducer to produce the pulse.

21. The method of claim 2, further comprising reducing interference from the first and second signal caused by an initial excitation of the transducer to produce the pulse.

22. The system of claim 12, wherein processing of the first and second signal further comprises reducing interference from the first and second signal caused by an initial excitation of the transducer to produce the pulse.

23. The system of claim 16, wherein the controller is further configured to reduce interference from the first and second signal caused by an initial excitation of the transducer to produce the pulse.

24. The method of claim 17, further comprising reducing interference from the first and second signal caused by an initial excitation of the transducer to produce the pulse.

25. A method for determining a size of an in vivo kidney stone, comprising the steps of:
(a) using an in vivo device comprising an acoustic transducer to detect:
  (i) a first signal generated in response to an interrogation pulse, the first signal comprising a first reflected acoustic wave that is reflected from a proximal surface of the in vivo kidney stone and a second reflected acoustic wave that is reflected from a distal surface of the in vivo kidney stone; and
  (ii) a second signal generated in response to the interrogation pulse, the second signal comprising a reflected acoustic wave that is reflected from a tissue supporting the distal surface of the in vivo kidney stone and that is only passed through an acoustical path from the support tissue to the acoustic transducer, the acoustical path positioned through a material alongside and outside the in vivo kidney stone and distal of the proximal surface of the kidney stone, the material comprising a fluid or a tissue which has a different composition than the support tissue; and
(b) processing the first and second signals to identify the first reflected acoustic wave and the acoustic wave reflected from the support tissue and processing the identified reflected acoustic waves to determine the size of the in vivo kidney stone, as a function of a time duration from a start of the first reflected acoustic wave to an end of the acoustic wave reflected from the support tissue and a speed of sound in the acoustical path material, and wherein the speed of sound in the acoustical path material is different than a speed of sound through the in vivo kidney stone.

26. The method of claim 25, further comprising reducing interference from the first and second signal caused by an initial excitation of the transducer to produce the pulse.

* * * * *